United States Patent
Mähr et al.

(10) Patent No.: US 6,169,223 B1
(45) Date of Patent: Jan. 2, 2001

(54) COMPRESS FOR MEDICAL TREATMENT

(75) Inventors: Rodolfo Mähr, Schaffhausen; Matthias Wendt, Neuhausen am Rheinfall, both of (CH)

(73) Assignee: Internationale Verbandstoff Fabrik Schaffhausen, Neuhausen Am Rheinfall (CH)

( * ) Notice: Under 35 U.S.C. 154(b), the term of this patent shall be extended for 0 days.

(21) Appl. No.: 09/245,661

(22) Filed: Feb. 8, 1999

(51) Int. Cl.⁷ .................................................. A61F 13/00
(52) U.S. Cl. ............................ 602/56; 604/366; 604/368; 604/372
(58) Field of Search ............................... 602/56; 604/366, 604/368, 372, 375, 378

(56) References Cited

U.S. PATENT DOCUMENTS

| | | |
|---|---|---|
| Re. 33,839 | 3/1992 | Chmelir et al. . |
| 3,967,623 | 7/1976 | Butterworth et al. . |
| 4,600,462 | 7/1986 | Watt . |
| 4,664,662 | 5/1987 | Webster . |
| 4,699,823 | 10/1987 | Kellenberger et al. . |
| 4,826,497 | 5/1989 | Marcus et al. . |
| 4,865,596 | 9/1989 | Weisman et al. . |
| 4,935,022 | 6/1990 | Lash et al. . |
| 4,938,756 | 7/1990 | Salek . |
| 4,994,037 | 2/1991 | Bernardin . |
| 5,069,908 | 12/1991 | Henley . |
| 5,147,646 | 9/1992 | Graham . |
| 5,171,238 | 12/1992 | Kajander . |
| 5,264,471 | 11/1993 | Chmelir . |
| 5,385,105 * | 1/1995 | Withers, Jr. et al. . |
| 5,409,771 | 4/1995 | Dahmen et al. . |
| 5,423,788 | 6/1995 | Rollins et al. . |
| 5,496,933 | 3/1996 | Kelkenberg . |
| 5,558,655 | 9/1996 | Jezzi et al. . |
| 5,567,478 | 10/1996 | Houben et al. . |
| 5,569,226 | 10/1996 | Cohen et al. . |
| 5,603,707 | 2/1997 | Trombetta et al. . |
| 5,610,220 | 3/1997 | Klimmek et al. . |
| 5,634,915 | 6/1997 | Österdahl . |
| 5,669,894 | 9/1997 | Goldman et al. . |
| 5,672,633 | 9/1997 | Brehm et al. . |
| 5,712,316 | 1/1998 | Dahmen et al. . |
| 5,721,295 | 2/1998 | Brüggemann et al. . |
| 5,736,595 | 4/1998 | Günther et al. . |
| 5,858,011 | 1/1999 | Brown et al. . |
| 5,885,516 | 3/1999 | Christensen . |

FOREIGN PATENT DOCUMENTS

| | | |
|---|---|---|
| 0031018 | 7/1981 | (EP) . |
| 0117351 | 9/1984 | (EP) . |
| 0342927 | 11/1989 | (EP) . |
| 0594034 | 4/1994 | (EP) . |
| 2044554 | 2/1971 | (FR) . |
| 2531627 | 2/1984 | (FR) . |
| 1192581 | 5/1970 | (GB) . |
| 7600779 | 7/1977 | (NL) . |
| WO 90/01913 | 3/1990 | (WO) . |

OTHER PUBLICATIONS

"The Tender Wet–Therapy For Spontaneous Wound Healing", IVF Brochure.

* cited by examiner

Primary Examiner—Michael A. Brown
Assistant Examiner—Lalita M Hamilton
(74) Attorney, Agent, or Firm—Dilworth & Barrese, LLP

(57) ABSTRACT

A medical compress for use in treating chronic wounds includes a non-woven textile fabricated from air laid fibers containing a superabsorbent material. The superabsorbent material is enclosed by a knitted mesh which can be formed to the shape of the wound. An irrigation solution is preferably contained by the compress to keep the wound irrigated and to encourage healing.

13 Claims, 3 Drawing Sheets

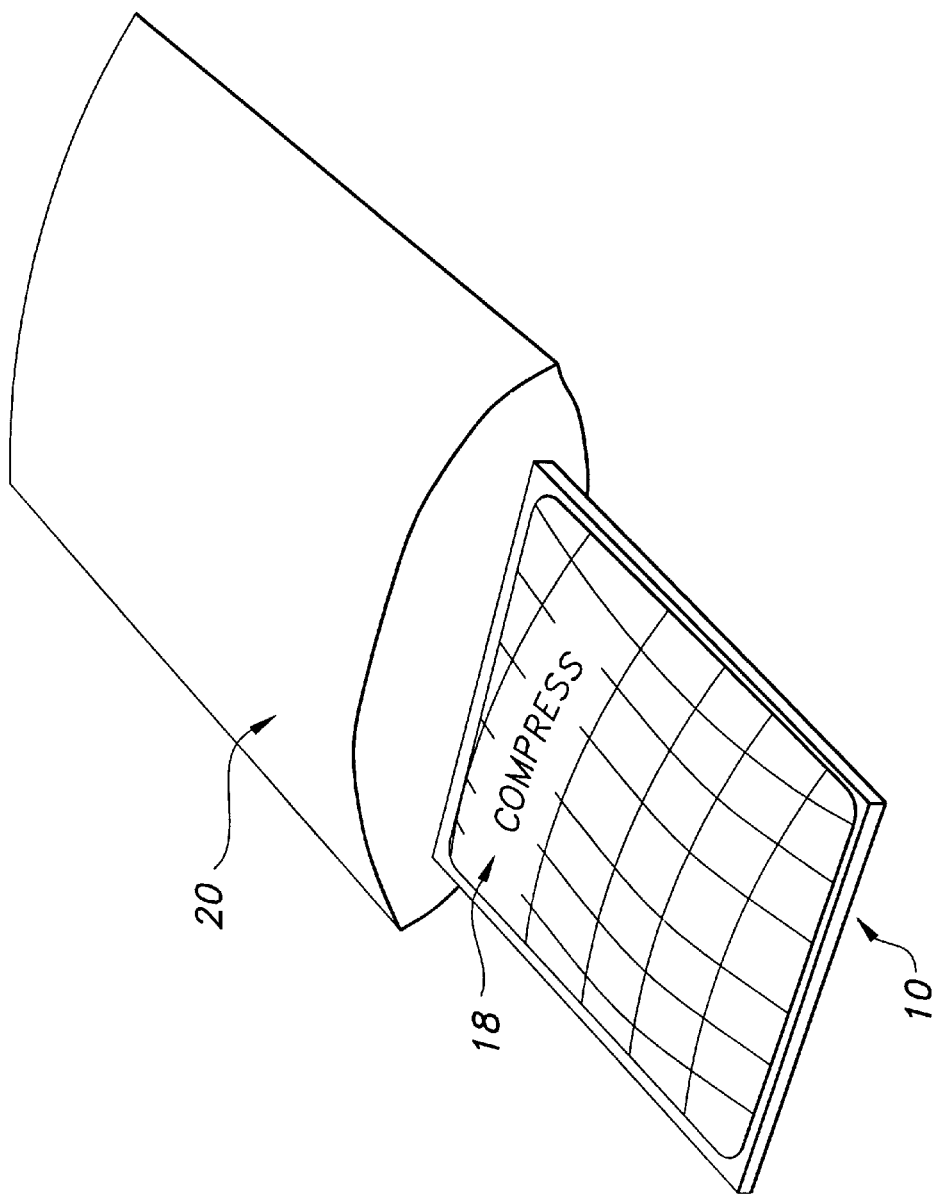

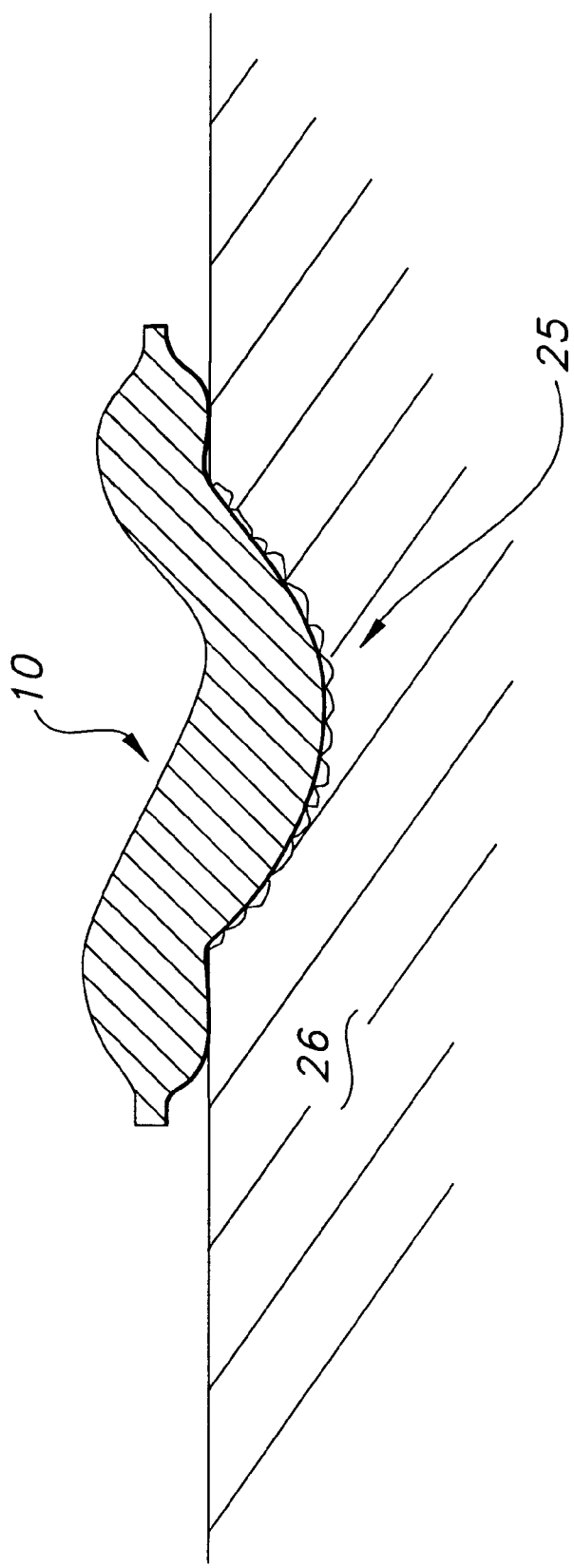

COMPRESS FOR MEDICAL TREATMENT

BACKGROUND

1. Technical Field

The present invention relates to a medical compress for the treatment of wounds in a wet or humid environment.

2. Background of Related Art

Wounds which do not heal with customary medical measures are termed chronic wounds. Frequently their development is promoted by various systemic diseases (diabetes mellitus and other metabolic disorders, arterial and venous vascular disorders, cardiac and circulatory disorders etc.)

The spread of germs and necroses favors the chronicity of the wounds. A possible cause for the progression of chronic wounds is the infiltration of necrotic of bacterial or other toxins into the surrounding tissues.

Every therapeutic concept for chronic wounds has the aim to support the self-healing power of the wound. In the first place, apart from treatment of the underlying disease and the exclusion of disturbing influences, the wound must be cleansed from necroses and toxins. In addition to surgical interventions (debridement) wet treatment with wet dressings has for decades taken the foremost place. Wet dressings usually imply in-hospital treatment of the patient, which considerably limits the realization of this therapy.

For spontaneous healing of a wound the most important substances required are proteins, lipids, vitamins and oxygen. If the supply of these substances is disturbed, the wound has a tendency to become chronic. In addition a number of external factors can delay spontaneous wound healing or make it impossible in this respect infections, but also excessive cooling or drying of the wound play a decisive part.

Growth factors play an important role as messengers for regulating almost all processes of wound healing. Cytokines are produced and released by a variety of cells and act on a variety of cell populations participating in wound healing.

In necrotic tissue toxins are liberated which infiltrate into the surrounding intact tissues. Thus, wound healing is impaired. If, for example, monocytes or macrophages are missing, the defense of infections becomes impossible. Blood vessels and nerve endings degenerate and recede. The result is progression of necrosis which can as a rule only be stopped with surgical debridement.

European Patent Publication EP 0,594,034 discloses a medical compress for treatment of wounds which includes a soakable body of superabsorbent material arranged in an outer cover layer. The compress is plastically deformable and can be formed into the profile of a wound. This publication is incorporated by reference herein.

A problem observed with superabsorbent materials formed into a fine textured, tight, laminate structure made from fabrics such as cellulose is gel blocking. Gel blocking occurs when gel formed in one region of the superabsorbent material physically interferes with absorption of fluid in a next region, thereby reducing absorption efficiency.

SUMMARY

A compress for the treatment of wounds is provided herein. The compress includes a non-woven textile fabricated from air-laid fibers containing a superabsorbent material and a cover for enclosing the non-woven textile. Optionally, a medical wound irrigating solution is contained in the medical compress.

The compress advantageously facilitates the healing of chronic wounds while providing improved comfort for the patient.

BRIEF DESCRIPTION OF THE DRAWINGS

Various embodiments are described below with reference to the drawings wherein:

FIG. 2 is an exploded perspective view showing the compress in combination with an envelope; and FIG. 3 is a sectional side view showing the compress applied to a wound.

DETAILED DESCRIPTION OF PREFERRED EMBODIMENT(S)

Figure 1:
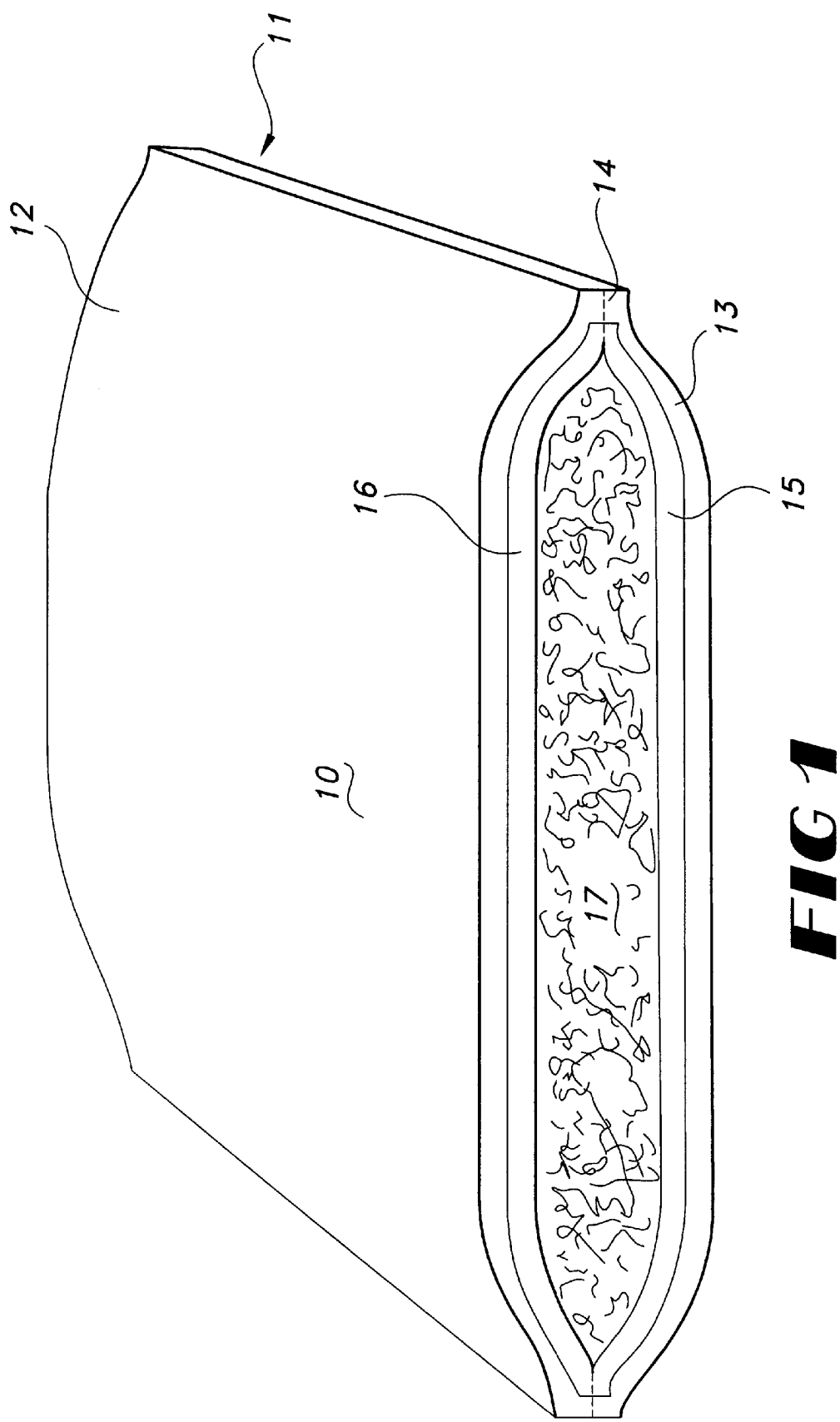
FIG. 1 is a sectional perspective view illustrating the compress of the present invention.

As used herein the terms top and bottom, and upper and lower, are used relative to each other.

Referring to FIG. 1 the medical compress 10 of the present invention includes an air laid textile 17 enclosed within a multipart cover 11. Cover 11 includes porous upper and lower exterior layers 12 and 13, respectively, which are preferably fabricated from a water permeable hydrophobic material. In a preferred embodiment upper and lower exterior layers 12 and 13 are knitted fabrics made from polypropylene threads. A suitable yarn for use in making the fabric of cover 10 is an airflow-textured multifilament yarn of pure polypropylene, preferably with a thread thickness of 170 dtex with 80 fibers or up to 85 dtex with 40 fibers. Because of the fabric's excellent permeability moisture is quickly transferred through the cover layer from the compress to the wound and from the wound to the compress whereas reacting of the superabsorbent material (see textile layer 17 discussed below) is substantially excluded. The yarn material absorbs only a small amount of moisture, usually less than about 0.1% by weight.

The top layer 12 preferably includes indicia 18 (FIG. 2) printed thereon for purposes of identification. Bottom layer 13 is the side to be brought into contact with the wound.

Top and bottom layers 12 and 13 are joined to each other at seam 14 which extends around the periphery of compress 10. Joining of layers 12 and 13 can be accomplished by heat bonding, adhesives or any other method suitable for the purposes described herein. The knitted fabric of cover 11 has in its unstressed state between 10 and 40 stitches per cm and stitch heights of from about 0.2 mm and 2.0 mm. The fabric deforms plastically, i.e. upon deformation of the compress the stitches of the fabric are reoriented such that its extensions are changed with little or no tendency to return to the fabric's initial shape or configuration.

Such fabric has an advantage over most conventional textile materials in that it is plastically deformable in all directions. It is possible for the compress 10 to be conformed to the contour of a wound. Even deep wounds can be filled by compress 10. Once formed and molded to a particular shape, compress 10 retains the shape.

Another advantage of the ability of compress 10 to be plastically conformed to a particular shape is that the mechanical forces exerted by the bandage located above the compress are not transferred to the wound.

Forces which can develop parallel to the surface of the wound created by the bandage will not shift the compress but cause the compress to be "rolled". A lateral force, which, for example, be caused by a bandage slightly out of place, causes a dislocation of the top surface of the compress without moving the bottom part of the compress. In this way, irritations of the wound, traumatic effects and pain can be avoided.

As mentioned above, the top and bottom exterior layers 12 and 13 are hydrophobic. If a hydrophilic material is used to fabricate the exterior layers 12 and 13, the hydrophilic material can be rendered hydrophobic by a suitable treatment such as, for example, coating it with wax or other suitable hydrophobic material.

The multipart cover 11 also includes lower interior layer 15 and upper interior layer 16.

Lower interior layer 15 is a layer of porous material which serves as a support for the air laid textile containing the superabsorbent material as described below. Lower interior layer 15 can be fabricated from any material suitable for the purposes described herein such as paper, cotton, rayon, nylon mesh, and the like. Cellulosic material is preferred. Lower interior layer 15 can be fabricated by any method suitable for the purposes described herein.

Upper interior layer 16 is preferably a smooth continuous sheet of material which is relatively impermeable or semi-permeable to water, blood and other body fluids so as to provide a moisture barrier. Suitable materials for use in fabricating upper interior layer 16 include polyethylene film, polypropylene film, and the like. Upper interior layer has a thickness preferably ranging from about 10 $\mu$m to about 100 $\mu$m.

The textile layer 17 is fabricated from air laid fibers containing superabsorbent material. The fibers can be selected from cellulose, polypropylene and polyethylene. Various superabsorbent materials are known in the art.

Superabsorbers are water insoluble, crosslinked polymers which, under swelling and the formation of hydrogels, are capable of absorbing large amounts of aqueous fluids and body liquids (such as urine, blood, etc.) and of retaining the absorbed amount of liquid under a certain pressure or load. Such materials are commonly used by incorporating them into sanitary articles such as diapers and sanitary napkins.

A significant feature of the present invention is that the fibers of the absorbent textile layer 17 are air laid. Methods for making an air laid textile are known in the art. The fibers are distributed by air currents into a three dimensional structure with random orientation within the textile web to provide a batting with isotropic properties. The air laid structure provides greater absorption efficiency as opposed to a laminated superabsorbent, which can suffer from gel blocking. Thus, the air laid textile layer allows a higher amount (2 to 4 fold increase) of the physiological irrigation solution to contact the wound site as compared with the compress described in EP 0,594,034B1. The air laid structure of the present invention significantly enhances the effect of the compress as described below, thereby leading to significantly faster wound healing.

The superabsorbent material can be a polymer derived from acrylic acid, methacrylic acid, 2-acrylamido-2-methylpropane sulfonic acid and the like. Most preferably the superabsorbent material is a sodium polyacrylate and/or sodium polymethacrylate, which can be prepared by neutralizing the acid groups of polyacrylic acid or polymethacrylic acid with sodium hydroxide. Unlike potassium polyacrylate or polymethacrylate the sodium derivative provides more comfort to the patient. Potassium polyacrylate or polymethacrylate can leak potassium ions into the extracellular fluid of the patient, which can lower the threshold of pain perception by their action on certain proteins. Use of a sodium polyacrylate or polymethacrylate overcomes this problem.

The absorbent textile layer 17 is preferably attached to the upper interior layer 16 by suitable means such as ultrasonic welding, adhesive bonding, and the like. Ultrasonic welding is preferred. The upper interior layer provides a barrier which prevents absorbed fluids from leading out to the upper surface of the compress 10 when, for example, the compress is applied to the wound or sore under light pressure.

The compress 10 is optionally prepared for use by pre-soaking the superabsorbent textile layer 17 with saline physiologic irrigation solution which contains the appropriate concentration of ions for the granulation cells of the skin epithel and for protecting the wound from dehydration. The irrigation solution is continuously released from the absorbent textile layer 17 thereby cleaning the would from toxins, cell debris, germs, etc. by osmotic forces. A preferred irrigation solution is available as Ringers solution.

Other medically useful substances can be incorporated into irrigation solution. For example, the irrigation solution can include antiseptics (e.g. povidone iodine), deodorants (such as etheric oils) and healing agents (e.g., allantoin) to accelerate healing.

As shown in FIG. 2 the compress 10, soaked in irrigation solution or in a dry state, can be packaged in an hermetically sealed, sterile envelope 20 which is impervious to microbes and moisture.

In use, the compress 10 will be removed from envelope 20, and applied to an open wound. As shown in FIG. 3, compress 10 will be conformed to the shape, or contour, of wound 25 in body tissue 26. A bandage (not shown) can be fastened over the compress 10 to keep the compress 10 in the desired position. The indicia 18 on the top surface of compress 10 can be used to distinguish between the top of compress 10 and the bottom.

The compress 10 is maintained in its position for a period of time determined by the attending physician. After the time period has elapsed the compress 10 is removed and the wound is examined to assess the progress of the healing. Optionally another compress 10 is applied to the wound in a similar manner and the processed is repeated until the wound has healed sufficiently.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A compress for the treatment of wounds which comprises:
   a) a non-woven textile fabricated from air laid fibers selected from the group consisting of cellulose, polypropylene and polyethylene fibers containing a superabsorbent material including sodium acrylate and/or sodium methacrylate polymer; and
   b) a cover for enclosing the textile, which includes an upper portion and a lower portion, the upper and lower portions being sealed around a periphery to define an interior closure in which the non-woven textile is positioned, wherein the lower portion of the cover includes a porous first exterior layer of a hydrophobic mesh and, in contact with the porous first exterior layer of hydrophobic mesh, a porous first interior layer in contact with a first side of the non-woven textile, and wherein the upper portion of the cover comprises a second exterior layer of hydrophobic mesh and, in contact with the second exterior layer of hydrophobic mesh, a moisture barrier second interior layer to which a second side of the non-woven textile is bonded.

2. The compress of claim 1 wherein the first and second exterior layers of hydrophobic mesh each comprise knitted polypropylene.

3. The compress of claim 1 wherein the second interior layer is fabricated from a polymer film which is impermeable or semipermeable to fluid.

4. The compress of claim 3 wherein said polymer film is selected from the group consisting of polyethylene film and polypropylene film.

5. The compress of claim 1 wherein the second exterior layer includes indicia.

6. The compress of claim 1 further including a wound irrigating solution absorbed into the superabsorbent material.

7. The compress of claim 6 wherein the irrigating solution includes a physiologic saline solution.

8. The compress of claim 7 wherein the irrigating solution further includes a component selected from the group consisting of antiseptic, deodorant and wound healing agent.

9. A wound treatment system including
   a) a medical compress which includes a non-woven textile fabricated from air laid fibers selected from the group consisting of cellulose, polypropylene and polyethylene fibers containing a superabsorbent material, and a cover for enclosing the textile, which includes an upper portion and a lower portion, the upper and lower portions being sealed around a periphery to define an interior closure in which the non-woven textile is positioned, wherein the lower portion of the cover includes a porous first exterior layer of a hydrophobic mesh and, in contact with the porous first exterior layer of hydrophobic mesh, a porous first interior layer in contact with a first side of the non-woven textile, and wherein the upper portion of the cover comprises a second exterior layer of hydrophobic mesh and, in contact with the second exterior layer of hydrophobic mesh, a second interior layer which is a polymer film relatively impermeable to fluids and to which a second side of the non-woven textile is bonded;
   b) a medical wound irrigation solution contained in the medical compress; and
   c) a wrapper for enclosing the medical compress, the wrapper being fabricated from a material impervious to both microorganisms and liquids.

10. The wound treatment system of claim 9 wherein the superabsorbent material includes sodium acrylate polymer.

11. The wound treatment system of claim 9 wherein the firs t and second exterior layers of hydrophobic mesh each comprise knitted polypropylene.

12. The wound treatment system of claim 9 wherein the second exterior layer includes indicia.

13. The wound treatment system of claim 9 wherein the second interior layer is polyethylene film.

* * * * *